United States Patent
Vanhove et al.

(10) Patent No.: US 12,258,577 B2
(45) Date of Patent: *Mar. 25, 2025

(54) METHOD EFFECTOR CELLS USING ANTI-CD127 ANTIBODIES FOR APPLICATIONS IN CELL THERAPY

(71) Applicants: OSE IMMUNOTHERAPEUTICS, Nantes (FR); ETABLISSEMENT FRANCAIS DU SANG, La Plaine St Denis (FR); ASSISTANCE PUBLIQUE—HOPITAUX DE PARIS, Paris (FR)

(72) Inventors: Bernard Vanhove, Reze (FR); Nicolas Poirier, Treillieres (FR); Sebastien Maury, Paris (FR); Jose Cohen, Paris (FR); Caroline Pilon, Saint Maurice (FR); Brigitte Birebent, Yebles (FR)

(73) Assignees: Ose Immunotherapeutics, Nantes (FR); Etablissement Francais Du Sang, La Plaine St Denis (FR); Assistance Publique—Hopitaux De Paris, Paris (FR)

( * ) Notice: Subject to any disclaimer, the term of this patent is extended or adjusted under 35 U.S.C. 154(b) by 840 days.

This patent is subject to a terminal disclaimer.

(21) Appl. No.: 16/643,550

(22) PCT Filed: Aug. 29, 2018

(86) PCT No.: PCT/EP2018/073253
§ 371 (c)(1),
(2) Date: Feb. 29, 2020

(87) PCT Pub. No.: WO2019/043065
PCT Pub. Date: Mar. 7, 2019

(65) Prior Publication Data
US 2020/0362300 A1  Nov. 19, 2020

(30) Foreign Application Priority Data
Aug. 29, 2017 (EP) .................................... 17306109

(51) Int. Cl.
*C12N 5/00* (2006.01)
*A61K 39/00* (2006.01)
*A61P 35/00* (2006.01)
*C07K 16/28* (2006.01)
*C12N 5/0783* (2010.01)

(52) U.S. Cl.
CPC ........ *C12N 5/0087* (2013.01); *A61K 39/4611* (2023.05); *A61K 39/4621* (2023.05); *A61K 39/464419* (2023.05); *A61P 35/00* (2018.01); *C07K 16/2866* (2013.01); *C12N 5/0636* (2013.01)

(58) Field of Classification Search
None
See application file for complete search history.

(56) References Cited

FOREIGN PATENT DOCUMENTS

| EP | 2583980 A1 | 4/2013 |
| EP | 2955196 A1 | 12/2015 |
| WO | WO 2017149394 A1 | 9/2017 |

OTHER PUBLICATIONS

Beliakova-Bethell, 2014, Cytometry, pp. 1-19.*
Basu, J. Visualized Experiments. pp. 1-4.*
Yeung, 2009, Anal. Biochem. vol. 389: 89-91.*
Dempsey, 2021, Cell. Mol. Bioeng. vol. 14: 267-277.*
International Patent Application No. PCT/EP2018/073253, International Search Report and Written Opinion dated Oct. 4, 2018, 29 pgs.
S. Touil et al.(2012), "Depletion of T regulatory cells through selection of CD127-positive cells results in a population enriched in memory T cells: implications for anti-tumor cell therapy", Haematologica, the Hematology Journal : Official Organ of the European Hematology Association, vol. 97, No. 11, Nov. 1, 2012 (Nov. 1, 2012), p. 1678-1685.
Natalia Marek et al.(2011), "The Time is Crucial for Ex Vivo Expansion of T Regulatory Cells for Therapy", Cell Transplantation, vol. 20, No. 11, Nov. 1, 2011 (Nov. 1, 2011), p. 1747-1758.
Volker Schirrmacher (2015), "Cancer-reactive memory T cells from bone marrow: Spontaneous induction and therapeutic potential (Review)", International Journal of Oncology, vol. 47, No. 6, Oct. 12, 2015 (Oct. 12, 2015), p. 2005-2016.
Robert F. Kudernatsch et al.(2014), "Human bone marrow contains a subset of quiescent early memory CD8 + T cells characterized by high CD127 expression and efflux capacity: Cellular immune response", European Journal of Immunology, vol. 44, No. 12, Oct. 27, 2014 (Oct. 27, 2014), p. 3532-3542.
Liu Weihong et al (2006), "CD127 expression inversely correlates with FoxP3 and suppressive function of human CD4(+) T reg cells", The Journal of Experimental Medicine, Rockefeller University Press, US, vol. 203, No. 7, Jul. 1, 2006 (Jul. 1, 2006), p. 1701-1711.

(Continued)

*Primary Examiner* — Amy E Juedes
(74) *Attorney, Agent, or Firm* — Cozen O'Connor

(57) ABSTRACT

The invention relates to methods and preparations for sorting out T effector cells from human leukocytes using anti-CD127 antibodies. Accordingly the invention relates to the use of anti-CD127 antibodies enabling discriminative depletion of subpopulations of Tregulatory cells expressing CD127+ at low levels in a population of human T lymphocytes in order to enable the use of the recovered selected cell preparations comprising essentially Teffector cells as lymphocytes and preferably devoid of Tregulatory cells, for improved efficacy in particular when administered to a patient for therapy.

Figure 1:
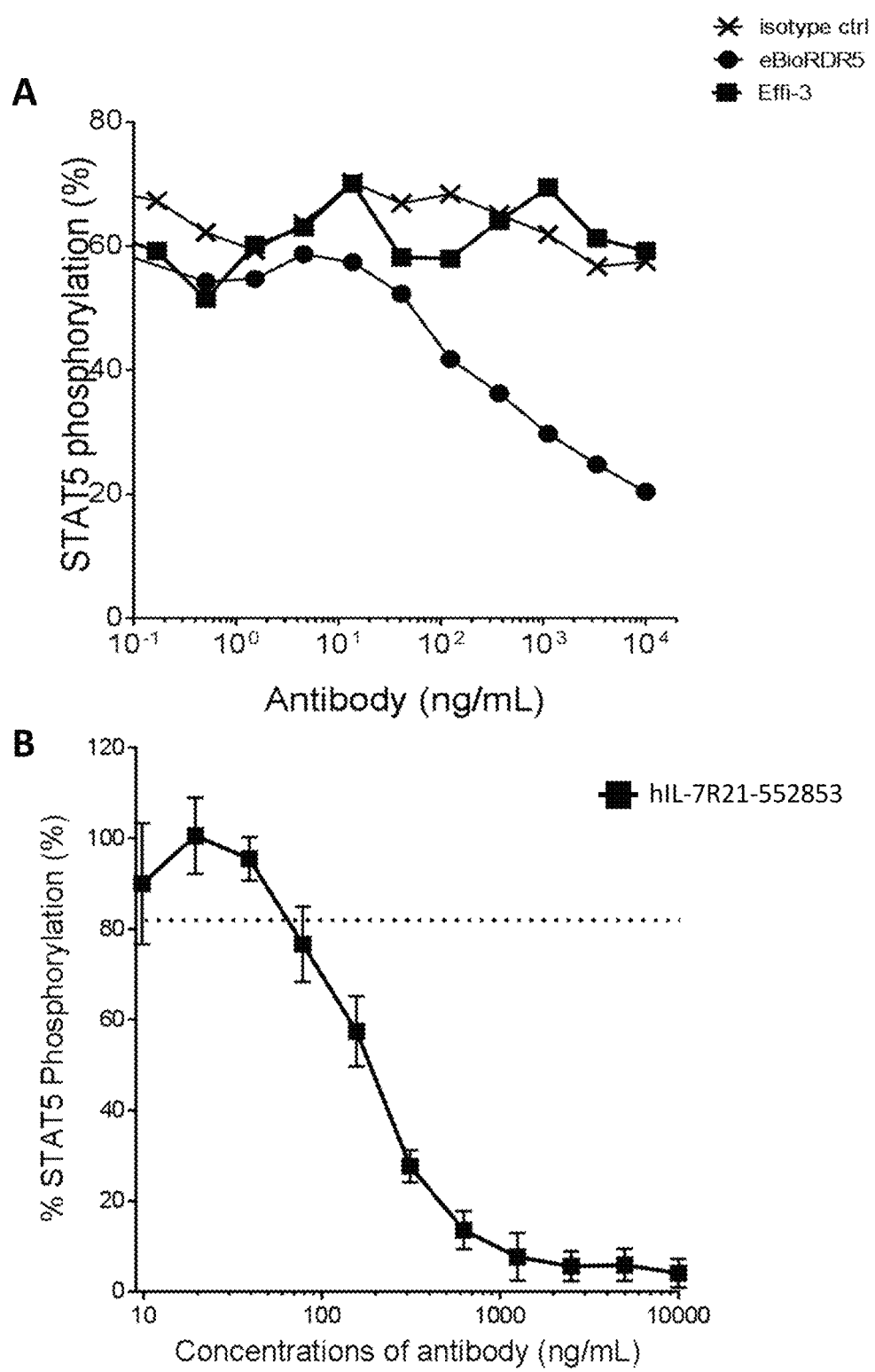

15 Claims, 2 Drawing Sheets
Specification includes a Sequence Listing.

(56) References Cited

OTHER PUBLICATIONS

Nicolas A. Giraldo et al.(2017), "Tumor-Infiltrating and Peripheral Blood T-cell Immunophenotypes Predict Early Relapse in Localized Clear Cell Renal Cell Carcinoma", Clinical Cancer Research, vol. 23, No. 15, Aug. 1, 2017 (Aug. 1, 2017), p. 4416-4428.
Sander Kelderman et al.(2016), "Antigen-specific TIL therapy for melanoma: A flexible platform for personalized cancer immunotherapy", European Journal of Immunology, vol. 46, No. 6, May 3, 2016 (May 3, 2016), p. 1351-1360.
Yosr Hicheri et al (2008), "Donor Regulatory T Cells Identified by FoxP3 Expression but Also by the Membranous CD4+CD127low/neg Phenotype Influence Graft-versus-tumor Effect After Donor Lymphocyte Infusion", Journal of Immunotherapy, vol. 31, No. 9, Nov. 1, 2008 (Nov. 1, 2008), p. 806-811.
International Patent Application No. PCT/EP2018/073253, International Preliminary Report on Patentability under Chapter II completed Sep. 4, 2019, 19 pgs.

\* cited by examiner

METHOD EFFECTOR CELLS USING ANTI-CD127 ANTIBODIES FOR APPLICATIONS IN CELL THERAPY

CROSS-REFERENCE TO RELATED APPLICATIONS

This application is a 35 U.S.C. § 371 filing of International Application No. PCT/EP2018/073253 filed Aug. 29, 2018, which claims the benefit of priority to European Patent Application No. 17306109.4 filed Aug. 29, 2017, each of which is incorporated herein by reference in its entirety.

The subject matter disclosed in the present application was developed, and the claimed invention was made, by one or more parties of a joint research agreement (JRA) between:
- OSE IMMUNOTHERAPEUTICS, Nantes, France;
- ETABLISSEMENT FRANCAIS DU SANG, La Plaine St Denis Cedex, France; and
- ASSISTANCEPUBLIQUE-HOPITAUX DE PARIS, Paris, France.

The JRA was in effect not later than the Aug. 29, 2017, effective filing date of the claimed invention, and the invention was made as a result of activities undertaken within the scope of the JRA.

The invention relates to methods and preparations for sorting out T effector cells from human leukocytes using anti-CD127 antibodies. Accordingly the invention relates to the use of anti-CD127 antibodies enabling discriminative depletion of subpopulations of Tregulatory cells expressing CD127+ at low levels in a population of human T lymphocytes in order to enable the use of the recovered selected cell preparations comprising essentially Teffector cells as lymphocytes and preferably devoid of Tregulatory cells, for improved efficacy in particular when administered to a patient for therapy. The applications of these methods and preparations encompass their use in the preparation of products comprising selectively depleted cell population essentially comprising Teffector cells intended for therapeutic purposes, in particular products for anti-tumor cell therapy including for adoptive cell transfer (ACT). The methods for sorting out Teff cells and the recovered preparations of the invention accordingly encompass a method for purifying Teffector cells from a population of human leukocytes comprised in a preparation of human cells, especially for enriching Teff cells from a cell preparation also comprising Treg cells, and encompass an enriched preparation of Teffector cells.

CD127 molecule is known as the extracellular domain of the alpha chain of the receptor for interleukin? (IL-7), especially the receptor for human IL-7 expressed on human cells (also designated human IL-7Ralpha or IL-7Ra having the sequence of Swiss Prot acession number P16871). "CD127-positive cells" (CD127+ cells) as used in the present invention designates cells expressing CD127 at their cell surface, in particular human cells expressing human CD127. In most cases, CD127-positive cells express CD127 in a complex forming the IL-7R (IL-7R-positive cells) and/or in a complex forming the TSLPR (TSLPR-positive cells). CD127 is expressed by various cells, including by both memory and naive T cells. CD127 is in particular expressed by effector T cells (Teff), including resting and memory T cells, and by immature B cells, and is also expressed by resting natural regulatory T cells (natural Treg), although at considerably lower levels. IL-7Rα is essential for promoting thymocyte differentiation and clonal expansion and homeostasis (proliferation, survival) of lymphocytes.

BACKGROUND

Donor lymphocyte infusions (DLI) can induce a graft-versus-tumor (GVT) effect in patients with a relapse of hematologic malignancies after allogeneic hematopoietic stem cell transplantation (HSCT). The anti-tumor effect of donor T cells was initially suggested by the increased risk of leukemia relapse observed in patients who received a T cell-depleted allogeneic stem cell transplant (Horowitz M M, et al. 1990).

In some cases, grafted patients never display any signs of alloreactivity, either following allogeneic HSCT or after DLI, despite incompatibility in human leukocyte antigens (HLA) and minor histocompatibility antigens (Martin P J. 1991). It has been suggested that this lack of responsiveness might be due to the presence in the infused lymphocytes of natural Treg resulting in an abrogated antitumor effect (Nishikawa H, Sakaguchi S. 2010). A proof of concept in mice demonstrated that Treg elimination from the transplant before infusion led to significantly accelerated alloreactivity, associated in man with a higher efficacy to fight leukemia cells (Cohen J L, Boyer O. 2006).

In human too, less Treg in the graft has been associated with more alloreactivity and a higher efficacy to fight cancer cells (Hicheri Y, et al. 2008), suggesting that eliminating Treg from the DLI product could improve their efficacy in patients with relapsed disease.

Eliminating Treg from the DLI product can be performed by cell sorting using different strategies:

1) by negative selection of Treg cells with high affinity anti-CD25 antibodies, CD25 being expressed on Treg cells and not on naïve Teff cells (Maury et al, 2010). A major drawback of this strategy is that Teff can also express high level of CD25 after activation, whereas activated Teff are important effector cells useful to fight cancer cells in vivo. The use of CD25 as a target to deplete Treg cells by negative selection thus suffers from the concomitant elimination of activated Teff cells.

2) Touil et al. have proposed to eliminate Treg cells from DLI preparations by use of a positive selection using a high-affinity anti-CD127 antibody, thus sorting out CD127+ cells that are mainly Teff cells (Touil et al., 2012). Since most Foxp3+ Treg also have weak surface expression of CD127, a major drawback of this strategy is that Treg cells do contaminate Teff cells preparations after positive cell sorting based on the CD127 marker.

In the present invention, investigating the use of mouse antibodies described in WO 2015/189302 in particular antibody designated EFFI7-3, the inventors identified the interest of this antibody and more particularly of derivatives thereof such as humanized antibodies designated as variants Effi-3 (identified as Effi-3-VH3VL3 and Effi-3-VH3VL4) (as described in WO 2015/189302), wherein said antibodies exhibit a moderate affinity against CD127, for sorting out Teff cells in order to carry out specific immunodepletion of cell populations, notably Treg cells. These antibodies with moderate affinity have nevertheless proved to be good binders of CD127+ cells and surprisingly presented a very high discriminating activity between Teff and Treg in a cell sorting process based on magnetic cell sorting, resulting experimentally in a robust depletion of more than 90% Treg cells from human blood cell preparations. These antibodies are also not competing with interleukin-7 for binding to the IL-7 receptor and therefore have no impact on the ability of sorted Teff cells to proliferate and mount an immune response. In other words, the sorted cells are not activated nor rendered anergic during and after carrying out a method according to the invention. These two features, a given binding activity and the absence of competition with IL-7, make of Effi-3 elected candidates for an efficient sorting out of Teff cells from a cell preparation depleted notably of Treg cells before T cell infusions in patients suffering from relapse of hematologic malignancies after allogenic hematopoietic stem cell transplantation (HSCT). They can also be useful for patients with a solid tumor receiving infusions of autologous ex-vivo expanded tumor-infiltrating cells (TILs), since Treg cells are known to heavily infiltrate tumors and to prevent action of anti-cancer Teff cells (Giraldo et al, 2017). They can also be useful for patients with solid or liquid tumors receiving infusions of Chimeric-Antigen Receptor T cells prepared from whole blood T cells originally containing Teff and Treg cells.

The invention accordingly concerns the use of humanized antibody in a process of sorting out subpopulation of Teffector cells from a preparation of cells, especially human cells such as human blood cells wherein the antibody is directed against the extracellular domain of the alpha chain of the receptor for interleukin? (IL-7), especially the receptor for human IL-7 expressed on human cells (also designated human IL-7Ralpha or IL-7Ra or CD127) and which does not interfere with the IL-7 signaling pathway. The antibodies are selected for their high binding capacity for human CD127+CD25− cells and/or for human CD127+CD25+ cells and moderate affinity for CD127, thereby enabling selective binding to Teffector cells with respect to other leukocytes expressing CD127 especially expressing low levels of CD127 such as CD4+CD25+Foxp3+CD127$^{low}$ regulatory T cells (Treg cells). The inventors have proved that these antibodies would be suitable in a process for in vitro sorting out Teff cells and shown in particular the efficacy of the antibody comprising the CDR sequences disclosed herein. The antibodies used can also be characterized by their capability to deplete CD127low Treg cells such as CD127lowFoxP3+ Treg cells. In a particular embodiment of the invention, the antibody enables purification of cell preparation wherein the resulting preparation shows depletion of CD127lowFoxP3+ Treg cells reaching a level of more than 90%, in particular more than 94%.

The invention relates to a method for sorting a cell preparation, such as a cell preparation derived from a biological fluid or tissue comprising human cells, especially human blood cells using an antibody against CD127 (the alpha chain of the interleukin-7 receptor), for discrimination between Treg and Teff cells and depletion of Treg cells. The obtained sorted cells depleted for Treg may be used for applications in cell therapies such as in cancerology. The obtained sorted cell preparation comprises Teff cells. In a particular embodiment the methods of the invention enable to recover a purified preparation of Teffector cells as a result of depletion or elimination of all other categories of leukocytes (Treg but also B cells, NK cells, monocytes). Purification of Teff cells may be enhanced in particular as disclosed below by the additional use of polyclonal human antibodies that prevents or reduce nonspecific interactions of the antibodies targeting CD127+ cells according to the invention. According to the methods and products (especially cell preparations) of the invention depletion means the elimination of at least part (i.e. at least a fraction) of Teg cells and advantageously elimination of at least 90% of Treg present in the starting preparation of cells. It also encompasses in a particular embodiment, elimination of at least a fraction of other leukocytes.

According to the invention, using the described antibodies effector CD127$^+$ T lymphocytes (Teff) can be separated from CD4+CD25+Foxp3+CD127$^{low}$ regulatory T cells (Treg) and accordingly recovered for applications in therapy, using the antibody of the invention. In the case of cancer, after infusion to a patient, purified Teff, i.e. Teff population depleted for Treg are expected to present a higher efficacy to kill target tumor cells. Examples of cell population suitable for treatment according to the invention and subsequent applications are donor lymphocyte infusions in patients with a relapse of hematologic malignancies after allogenic hematopoietic stem cell transplantation (HSCT), for infusions of autologous tumor-infiltrating cells (TILs) in patients with a solid tumor and or genetically modified cancer-specific T cells such as cells used for infusion of Chimeric-Antigen Receptor T cells (CAR transduced T cells) in patients with solid or liquid tumors.

Other therapeutic targets for the preparation of cell preparations depleted for Treg population obtained according to the invention or depleted for Treg population and for other leukocytes obtained according to the invention, are chronic infectious diseases such as chronic infections due to bacteria, parasites, protozoans, yeasts or viruses.

The invention accordingly concerns a method for in vitro sorting out Teffector cells from a preparation of cells, in particular a preparation of cells obtained from a biological fluid or tissue wherein the preparation of cells comprises human cells especially human blood cells, wherein the method comprises the step of:

a. contacting the cell preparation with an antibody specifically binding to CD127 and having a moderate affinity for CD127 and selectively binding to Teffector cells present in the cell preparation, b. selectively sorting out said Teffector cells and recovering the cell preparation depleted for at least Treg cells;

in particular wherein the antibody specifically binding to CD127 does not interfere with the IL-7 signaling pathway.

In a particular embodiment, the invention concerns a method for in vitro sorting out Teffector cells from a preparation of cells, in particular a preparation of cells obtained from a biological fluid or tissue wherein the preparation of cells comprises human cells especially human blood cells, wherein the method comprises the step of:

a. contacting the cell preparation with an antibody specifically binding to CD127 and having a moderate affinity for CD127 and selectively binding to Teffector cells present in the cell preparation, and which does not interfere with the IL-7 signaling pathway;

b. selectively sorting out said Teffector cells and recovering the cell preparation depleted for at least Treg cells.

In a particular embodiment the thus defined method is a method for purification of Teff cells wherein purification is obtained by sorting out Teff cells from an originally provided cell preparation. Purification of Teff cells accordingly encompasses enriching the starting preparation of cells for Teff cells with respect to other T cells, as a result of depletion of Treg cells wherein depletion reaches 90% or more of said Treg cells, and possibly reaches elimination of 99% or more of Treg cells. The level of depletion in Treg cells or the level of purity of Teff cells may be determined by flow cytometry using fluorescence-activated cell sorting (FACS) analysis according to methods well known from the person skilled in the art. Accordingly the expression "depleted for Treg cells" encompasses the depletion of at least part (a fraction) of Treg cells, in particular of at least 90% of Treg cells and in a more particular embodiment depletion of 99% of Treg cells. It also encompasses the depletion of the cell preparation for at least Treg cells and thus encompasses the depletion of Treg cells and of other cells that are CD127+ cells such as leukocytes to achieve higher purification of Teff cells.

The preparation of cells provided for treatment according to the methods of sorting out Teff cells of the invention is a preparation that comprises T lymphocytes, in particular a preparation that comprises T regulatory cells and T effector cells. The method of the invention is intended and suitable to enrich the cell preparation for T effector cells with respect to T regulatory cells and is accordingly designed to effectively deplete the T regulatory cell population. The sorted cells recovered from the process comprises Teff cells, advantageously comprise essentially Teff cells. In a particular embodiment the sorted cells consist of Teff cells. The preparation of cells to be treated is a preparation comprising human leukocytes, in particular lymphocytes. In addition to T cells such as Teff and Treg, the preparation of cells to be treated may comprise any of the following cells types: B lymphocytes, NK cells and monocytes. The method of the invention which enables sorting out Teff cells enables depletion of other subpopulations of leukocytes i.e., Treg, and any of B lymphocytes, NK cells or monocytes. In a particular embodiment, the sorted preparation of cells obtained when carrying out the methods of the invention has a level of purity for CD127+cells, in particular Teff cells of more than 70%, especially more than 80% or more than 85%.

The preparation of cells for carrying out the methods of the invention may be a natural cell preparation such as a cell preparation obtained, in particular purified from a biological fluid or tissue. It may alternatively be a previously treated cell preparation such as a cell preparation formulated for administration to a human patient or a preparation that comprises genetically modified cells. The cell preparation is advantageously a preparation of human cells, especially a preparation of human blood cells.

The cell preparation is depleted for Treg cells according to the step of sorting out Teff cells in the methods of the invention. Accordingly sorting out targets primarily but not exclusively the depletion of Treg cells of the preparation wherein said Treg cells express low level of CD127, such as CD4+CD25+Foxp3+CD127$^{low}$ regulatory T cells. By contrast T effector cells (Teff) are retrieved using the anti-CD127 antibody used in the method of the invention and possibly retrieved as a subpopulation devoid of other leukocytes (i.e., purified).

In a particular embodiment, the cell preparation is a human blood cell preparation. In a further particular embodiment, the cell preparation is a preparation of hematopoietic stem cells for transplantation (HSCT) or is expanded tumor-infiltrating cells (TILs) or is genetically modified cancer-specific T cells such as cells used for Chimeric-Antigen Receptor T cells (CART). Accordingly the invention relates to a method of sorting out these particular cell preparations and also relates to sorted cells preparation of HSCT, TILs or CART comprising or consisting of Teff and depleted for at least Treg cells in accordance with the present description.

The anti-CD127 antibody used in the process of the invention is "specific" for its CD127 target or "binds specifically" to its target if it exhibits a threshold level of binding activity and/or it does not significantly cross-react with known related molecules. One skilled in the art can readily determine said binding capacity. The anti-CD127 antibody used according to the invention is also "selective" to the extent that it targets essentially Teff cells by contrast to Treg.

In a particular embodiment, the anti-CD127 antibody used in a method according to the invention has at least one of the following properties: it is neither an agonist nor an antagonist of the IL-7R signaling pathway induced by IL-7; and/or it does not interfere with the IL-7 signaling pathway; and/or it does not compete with IL-7 for the binding to CD127; and/or it does not inhibit or enhance IL-7R signaling pathway induced by the binding of IL-7 to CD127; in a more particular embodiment of the invention, the anti-CD127 antibody has at least 2 of the recited properties, and in a most particular embodiment, the anti-CD127 antibody has at least three of the recited properties. In a particular embodiment, an anti-CD127 antibody has the four recited properties. These properties may be determined according to the methods described in the examples of the present invention, in particular by assessing STAT5 phosphorylation in presence of an anti-CD127 antibody and IL-7, in particular by flow cytometry or ELISA. In presence of an antibody which does not interfere with the IL-7 signaling pathway, the phosphorylation of STAT5 shouldn't substantially differ as compared to an assay with a control without an antibody or in presence of a negative control antibody (i.e. which does not bind to a molecule directly involved in the IL-7 signaling pathway).

In a particular embodiment, an antibody which has a moderate affinity for CD127 is an antibody with a $K_D$ value for CD127 comprised between $10^{-6}$ M and $9.10^{-9}$ M, more particularly comprised between $10^{-7}$ M and $9.10^{-9}$ M, more particularly comprised between $10^{-7}$ M and lower than $9.10^{-9}$ M, and most particularly comprised between $10^{-7}$ M and $10^{-9}$ M The term comprised used therein should be understood as including the recited upper and lower limits of the range (e.g. in the first embodiment, $10^{-6}$ M and $9.10^{-9}$ are encompassed within the recited range). On the contrary, a high affinity antibody may be defined as having a $K_D$ value for CD127 over $10^{-10}$ M. An antibody with a moderate binding affinity for CD127 is suitable for sorting out the T cell populations as described here above, but presents the advantage of being easily stripped from the cell after carrying out the sorting of the T cells, on the contrary to an antibody with a high affinity for CD127.

Antibodies specific for binding to human CD127 and selective for Teff cells that are suitable to carry out the invention are designated Effi 3 and characterized as follows by their amino acid sequences:

(i) Effi3, which comprises the following CDR sequences:
in the heavy chain, the CDRs of the VH3 heavy chain disclosed herein as sequence of SEQ ID No2, in particular CDRs of VH3-CDR1, VH3-CDR2 and VH3-CDR3 comprising or consisting of the sequences of SEQ ID No14, 16 and 18, respectively and,
in the light chain, the CDRs of the VL3 or of the VL4 light chain disclosed herein as sequences of SEQ ID No No4 and 6, respectively, in particular with VL3-CDR1, VL3/4-CDR2 and VL3/4-CDR3 comprising or consisting of the sequences of SEQ ID No20, 22 and 24 respectively, or CDRs of VL4-CDR1, VL3/4-CDR2 and VL3/4-CDR3 comprising or consisting of the sequences of SEQ ID No26, 22 and 24 respectively.

and in particular
(ii) Effi3 which is illustrated by the following embodiments of its variable heavy and light chains:
A heavy chain variable domain designated Effi3-VH3 (or VH3) which may contain additionally a signal peptide sequence (comprising or consisting of sequence of SEQ ID No2 in Table 5, or a variant comprising or consisting of SEQ ID No8 which includes a signal peptide), which comprises CDRs designated as VH3-CDR1, VH3-CDR2, VH3-CDR3; and for the variant designated Effi3-VH3VL3, either a light chain variable domain designated Effi3-VL3 or VL3 (comprising or consisting of sequence of SEQ ID No4 in Table 5, or a variant comprising or consisting of SEQ ID No10 which includes a signal peptide), which comprises CDRs designated as VL3-CDR1, VL3/4-CDR2, VL3/4-CDR3;

or, for the variant designated Effi3-VH3VL4, either a light chain variable domain designated Effi3-VL4 (or VL4) comprising or consisting of sequence of SEQ ID No6 in Table 5, or a variant comprising or consisting of SEQ ID No12 which includes a signal peptide, which comprises CDRs designated as VL4-CDR1, VL3/4-CDR2, VL3/4-CDR3.

In a preferred embodiment the antibody is the antibody designated Effi-3VH3VL3 as defined herein, wherein its light chain variable domain comprises or consists of the sequence of SEQ ID No.4 or 10.

Such an antibody, comprising the recited CDRs, has the ability to have a moderate affinity for CD127. More particularly, such an antibody has a $K_D$ value for CD127 comprised between $10^{-6}$ M and $9.10^{-9}$ M, more particularly comprised between $10^{-7}$ M and $9.10^{-9}$ M, more particularly comprised between $10^{-7}$ M and lower than $9.10^{-9}$ M, and most particularly comprised between $10^{-7}$ M and $10^{-9}$ M. The term comprised used therein should be understood as including the recited upper and lower limits of the range (e.g. in the first embodiment, $10^{-6}$ M and $9.10^{-9}$ are encompassed within the recited range). The moderate affinity of such an antibody for CD127 is illustrated in the examples of the invention.

As recited herein, such an antibody may have the ability not to interfere with the IL-7 signaling pathway. In other words, such an antibody has at least one of the following properties: it is neither an agonist nor an antagonist of the IL-7R signaling pathway induced by IL-7; and/or it does not interfere with the IL-7 signaling pathway; and/or it does not compete with IL-7 for the binding to CD127; and/or it does not inhibit or enhance IL-7R signaling pathway induced by the binding of IL-7 to CD127; in a more particular embodiment of the invention, the anti-CD127 antibody has at least 2 of the recited properties, and in a most particular embodiment, the anti-CD127 antibody has at least three of the recited properties. In a particular embodiment, an anti-CD127 antibody has the four recited properties. The examples of the invention illustrate the ability of such an antibody not to interfere with the IL-7 signaling pathway. An antibody which has the ability not to interfere with the IL-7 signaling pathway induced by IL-7 may also be defined as an antibody which does not induce by more than 20%, and which does not inhibit by more than 20% the phosphorylation of STATS as compared with the phosphorylation of STATS in presence of a control, e.g. an antibody which is known not to interfere with the IL-7R signaling pathway nor with CD127, or without any antibody. In a more particular embodiment, the antibody does not induce or inhibit by more than 10% STATS phosphorylation as compared to a control. The STATS phosphorylation may be assessed according to methods known in the art, or by the method disclosed in the examples of the invention.

In an embodiment of the methods of the invention, the anti-CD127 antibody is biotinylated or is otherwise marked in order to enable staining.

According to a particular embodiment of the invention, the method of sorting out Teff cells according to the invention is carried out using magnetic cell sorting, in particular using magnetic beads carrying the anti-CD127 antibodies.

According to a preferred embodiment of the invention, cell sorting is performed until 90% or more than 90%, in particular more than 94%, more particularly more than 99% of Treg cells are depleted from the preparation of cells. Otherwise stated 90% or more of the Treg cells estimated to be present in the cell preparation provided for treatment according to the methods of the invention are separated from the preparation it exists in originally. Techniques for measurement of the level of cell sorting are disclosed in the Examples.

In a particular embodiment of the methods, anti-CD127 antibodies as disclosed herein are provided together with a composition that comprises polyclonal immunoglobulins, especially polyclonal human immunoglobulins, suitable for reducing nonspecific interactions of anti-CD127 antibodies with target Teff cells. Examples of polyclonal immunoglobulins are described hereafter as commercial preparations.

The invention also concerns a preparation comprising or consisting of Teffector cells depleted for at least Tregulatory cells population. Such preparation comprises or consists in Teffector cells in which the IL-7 signaling pathway may not be induced nor inhibited, and which is substantially free of anti-CD127 antibodies used for sorting out the Teffector cells. For assessing if the IL-7 signaling pathway is induced or inhibited, the signaling pathway related to IL-7 in Teffector cells depleted for at least Tregulatory cells population may be compared with the same signaling pathway in T cells isolated but not sorted out, or sorted out according to methods of the prior art. As examples, the phosphorylation level of STATS and/or Pi3K may be assessed, the cell surface expression of CD127 may be compared, the level of transcription of genes known to be induced or inhibited when the IL-7 signaling pathway is activated or inhibited may be measured. The presence of anti-CD127 antibodies may be assessed by using a second antibody which recognized the anti-CD127 antibody and which is marked for staining.

Such a preparation of Teffector cells depleted in at least Tregulatory cells population is particularly suitable for a subsequent use in adoptive T cell therapy, including but not limited to TCRs (T Cell Receptors technology), CARs (Chimeric Antigen Receptors), TILs (expanded Tumor-Infiltrating cells). Adoptive T cell therapy is the transfer of T lymphocytes to a subject in need thereof for the therapy or the prevention of a disease or a condition. Such a preparation of Teffector cells depleted in at least Tregulatory cells population is particularly suitable for a subsequent use in hematopoietic stem cells transplantation.

In a particular embodiment, such a preparation of Teffector cells depleted in at least Tregulatory cells population comprises more than 85% of Teffector cells, in particular more than 86% of Teffector cells. In a particular embodiment, the preparation of Teffector cells depleted in at least Tregulatory cells population comprises less than 90%, in particular less than 95%, of Tregulatory cells as compared to the population of Tregulatory cells in the sample freshly obtained from a patient, and before carrying out the method of the invention.

The invention also concerns a preparation comprising or consisting of Teffector cells depleted for at least Tregulatory cells population, said preparation being prepared according to any method disclosed therein.

Compositions or sets or compounds associating in admixture or as separate compounds for simultaneous use in the methods of the invention, anti-CD127 antibodies disclosed herein and polyclonal immunoglobulins may be obtained using the following preparations of immunoglobulins: human polyclonal immunoglobulins such as commercial preparations available under the names of: Tegeline (Lfb-Biomedicaments), Carimune (BDI Pharma), Flebogamma (Grifols), Gammagard Liquid (Baxter), Gammagard SD LIGA (Baxter), Gammagard SD (Baxter), Gammaked (BDI Pharma), Gammaplex (BPL Bio Products Laboratory), Gamunex (Grifols), Octagam (Octapharma), Privigen (CSL Behring).

In an embodiment the invention relates to the use of the methods and compositions or sets of compounds disclosed, for the preparation of treated human cells, especially blood cells, depleted for Treg cells, in particular for the preparation of a Treg depleted population of hematopoietic stem cells for transplantation (HSCT) or T cells for Adpotive T Cell Therapy, in particular expanded tumor-infiltrating cells (TILs) or genetically modified cancer-specific T cells such as cells defined as Chimeric-Antigen Receptor T cells (CART).

In an embodiment the invention relates to the use of the methods and compositions or sets of compounds disclosed, for the preparation of treated/sorted cells, in particular treated human cells, especially blood cells, comprising or consisting of Teff cells and depleted for at least Treg cells wherein the cell preparation is suitable for treatment of solid or liquid tumor in a human patient or suitable for treatment of chronic infections by a pathogen selected among bacteria, parasites, protozoans, yeasts and viruses in a human patient.

Diseases that may be subject to T cell therapies with a preparation of cells treated (i.e. sorted) according to the invention include chronic infectious diseases such as those involving bacteria in particular bacteria of genus borrelia associated with Lime disease, or genus rickettsia, bartonella, mycoplasma, chlamydia, chlamydophila, coxiella, streptoccus, ehrlichia, anaplamsa . . . , or involving parasites (such as nematodes, cestodes, trematodes . . . ), or protozoans (such as babesia, amibes, plasmodium . . . ), yeasts (such as candida), or viruses (EBV, CMV, HHV, HIV . . . ).

The invention also relates to a preparation of treated (or sorted) human cells especially blood cells, comprising or consisting of Teff cells and depleted for Treg cells, in particular a preparation of Teff cells depleted for at least Treg which is obtained from a population of hematopoietic stem cells for transplantation (HSCT) or from T cells for Adoptive T cell Therapy, in particular T cells from expanded tumor-infiltrating cells (TILs) or from genetically modified cancer-specific T cells such as Chimeric-Antigen Receptor T cells (CART), wherein the Treg depletion is advantageously 90% or more. Depletion of Treg cells and possibly other leukocytes has been defined above and is illustrated in the Examples and accordingly encompasses elimination of at least a fraction of Treg such as at least 90% of the Treg cells. According to a particular embodiment the level of purity of the obtained CD127+ cells, in particular Teff cells, is 70% or more, in particular 80% or 85% or more.

In particular, said preparation of treated (or sorted) human cells depleted for Treg cells, or for Treg and other leukocytes especially blood cells, has been prepared by carrying out the method of sorting out Teff cells according to the invention or using a composition or a set of compounds according to the invention.

The method of sorting out Teff cells according to the invention is used for the preparation of cells having therapeutic interest for administration to patients.

Accordingly the invention relates to a depleted cell preparation as defined herein, that comprises or consists of Teff cells and is depleted for at least Treg cells and possibly for other leukocytes, in particular a preparation obtained after carrying out the method of the invention, for use in treating a human patient against hematologic malignancies, especially against relapsing hematologic cancer wherein a population of hematopoietic stem cells for transplantation (HSCT) depleted for at least Treg is administered to the patient.

In another embodiment, the invention relates to a depleted cell preparation as defined herein that comprises or consists of Teff cells and is depleted for at least Treg cells and possibly for other leukocytes, in particular a preparation obtained after carrying out the method of the invention, for use in treating a human patient against solid tumor, wherein T cells for Adoptive T cell therapy, in particular expanded tumor-infiltrating cells (TILs) depleted for at least Treg cells are administered to the patient or for use against solid or liquid tumor, and/or wherein genetically modified cancer-specific T cells such as Chimeric-Antigen Receptor T cells (CART) depleted for at least Treg cells population are administered to the patient.

In another embodiment, the invention relates to a preparation as defined, in particular a preparation obtained after carrying out the method of the invention, for use in treating a chronic infection in a human patient wherein the pathogen is selected among bacteria, parasites, protozoans, yeasts and viruses as disclosed herein.

The invention also relates to a combination product comprising (i) a preparation of cells obtained after carrying out the method according to the invention or using a composition or a set of compounds according to the invention or a preparation of cells according to the invention and (ii) a compound of therapeutic interest such as an anti-cancer agent or a T cell activator. An anti-cancer agent may be selected among the group comprising chemotherapeutic agents (such as chlorambucil, bendamustine, dexamethasome and lenalidomide), radiotherapeutic agents or immunotherapeutic agents. An immunotherapeutic agent in the context of invention may be selected among the group comprising therapeutic vaccines, with peptides, proteins or neoantigen specific of the tumor cell lineages (WT1 MUC1, CD138, BCMA, CD138, and CS1) or gene-transduced tumor cell vaccine (GVAX) platform, monoclonal antibodies directed against specific markers of tumor cells (anti-CD20, anti-CD138, anti-CD56, CD40, BAFF, CD38, CD30), proteasome inhibitors such as SLAMF7, anti-drug conjugate such as Inotuzumab (CD33) plus ozogamicin, Bispecific T cell engagers (BiTEs) and immune checkpoint blockers or immune checkpoint activators such as antibodies against CTLA4, PD1, PDL1, OX40L, CD80, CD86, SIRPa, 41BBL, ICOSL Tim3, Lag-3 and BTLA. In a particular embodiment of the invention, the combination product comprises a preparation of cells according to the invention and a compound which has a positive effect on T cell activation and/or proliferation.

Additional features details and embodiments will be apparent from the examples which follow and from the figures.

LEGEND OF THE FIGURES

FIG. 1: A. T lymphocytes from the blood of human healthy volunteers were mixed with the indicated concentration of Effi-3 or eBIORDR5 antibodies for 15 min and then with 10 ng/ml recombinant IL-7 for 15 min., fixed and permeabilized and analyzed by flow cytometry with a fluorescent antibody against the phosphorylated form of STAT-5. B. T lymphocytes from the blood of human healthy volunteers were mixed with the indicated concentration of hIL7R-M21 commercial antibody (BD) for 15 min and then with 0.1 ng/ml recombinant IL-7 for 15 min., fixed and permeabilized and analyzed by flow cytometry with a fluorescent antibody against the phosphorylated form of STAT-5.

Figure 2:
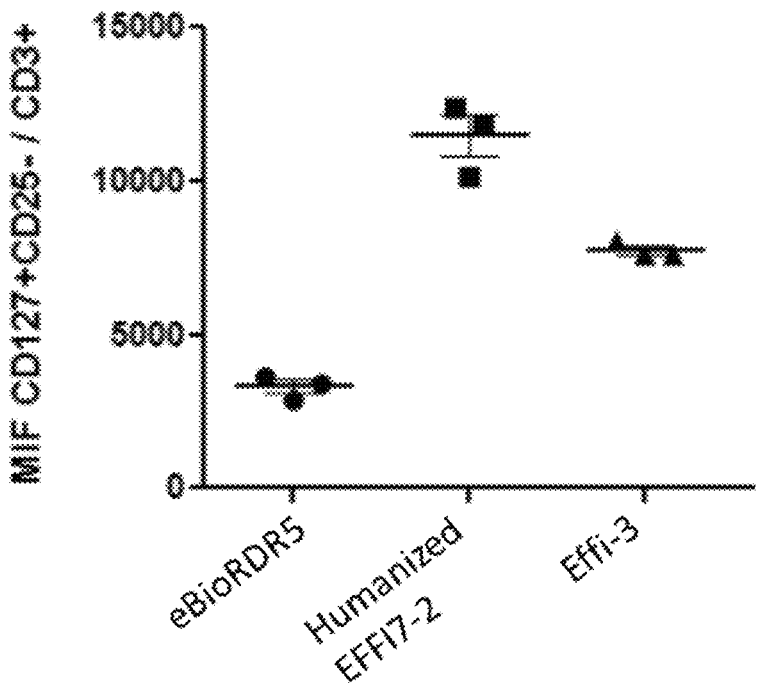

FIG. 2: Mean fluorescence intensity (MFI) measured by flow cytometry of the binding of anti-CD127 antibodies on CD3+ CD25- T cells from blood from three human healthy volunteers.

Figure 3:
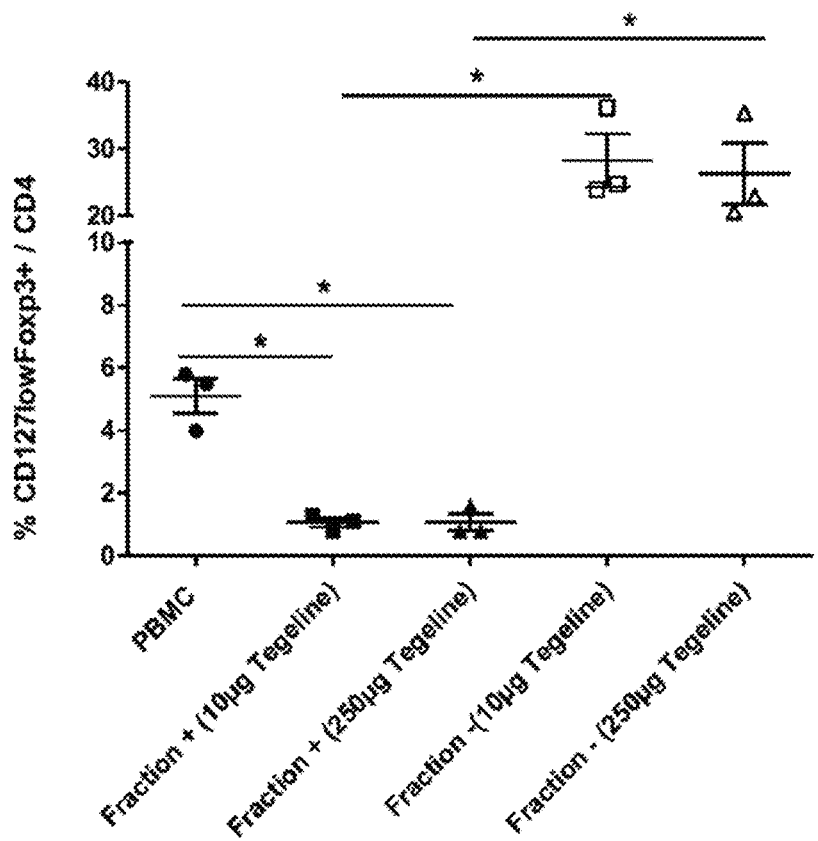

FIG. 3: % CD127$^{low}$FoxP3$^+$ within the CD4+ compartment in PBMC or in positive and negative fractions after Miltenyi magnetic beads sorting of CD127+ cells using the biotinylated Effi-3 antibody with 10 and 250 μg Tegeline. Three sorting from 3 individual donors are shown. * p<0.05.

EXAMPLES

Results

Antibody Selection Based on Binding Capacities

Several antibodies from mouse hybridoma have been generated by classical immunization techniques. The affinity of the resulting antibodies has been measured by Biacore and the binding capacity on target cells evaluated by flow cytometry on human blood cells. Clones EFFI7-1 and EFFI7-3 showed the highest binding capacity while not the highest affinity (Table 1).

TABLE 1 mouse antibodies have been derived by immunization and classical hybridoma technology, and their affinity has been measured by plasmon resonance (Biacore). In parallel, purified antibodies at a concentration of 0.03 micrograms/$10^6$ target cells were used to stain human blood cells from a healthy volunteer by flow cytometry. Data are % of positive cells in CD3+ cells.

| Antibody | KD (M) | Target cell recognition (% CD127+CD25- cells) |
|---|---|---|
| Effi7-1 | 1.59 × $10^{-8}$ | 72 |
| Effi7-2 | 6.24 × $10^{-10}$ | 55 |
| Effi7-3 | 0.65 × $10^{-8}$ | 84 |
| Effi7-4 | 0.65 × $10^{-8}$ | 39 |
| Effi7-5 | 2.5 × $10^{-9}$ | 57 |
| Effi7-9 | 4.2 × $10^{-9}$ | 15 |
| Effi7-12 | 2 × $10^{-9}$ | 46 |
| Effi7-13 | 1.3 × $10^{-9}$ | 54 |

Clones EFFI7-1 and EFFI7-3 were then compared by flow cytometry with the commercial clone eBIORDR5 (Invitrogen Catalog #: 14-1278-82), using three human donors. The data demonstrated that EFFI7-1 and EFFI7-3 bound to CD3$^+$ cells with a mean fluorescence intensity of 8229+/−1124 (SEM) and 9819+/−551, respectively and that eBIORDR5 bound to CD3+ cells with a mean fluorescence intensity of 4145 +/−843. Therefore, EFFI7-3 demonstrated a stronger binding than EFFI7-1 and than eBIORDR5. To prepare further developments, EFFI7-3 has been humanized to become "Effi3-VH3VL3" or "Effi3-VH3VL4", or "Effi-3", an IgG1 CDR-grafted humanized antibody. Effi3-VH3VL3 is described herein.

Affinity-Binding to CD127 Protein

The affinity for CD127 of the antibody Effi3-VH3L3, and antibodies of the prior art (eBioRDR5 and hIL-7R-M21) has been assessed using Biacore technology (CD127-Fc (Sino Biological; 100 μg/mL; 10 μL), Effi3-VH3L3 (4.35 mg/mL; 150 kDa, 30 μL), eBioRDR5 (CD127 Monoclonal Antibody, eBioscience™ from Invitrogen/Thermo Fisher Scientific catalog # 14-1278-82; 0.025 mg/mL; 150 kDa; 50 μL)). CD127-Fc was immobilized by amine coupling on a CM5 chip. The carboxylic groups were esterified by injection of an NHS/EDC mix for 7 min. The CD127-Fc proteins diluted to 20 μg/ml in Na acetate buffer pH 4.6 were injected until an SPR signal of 500 RU was obtained. Free reactive sites were inactivated by injection of 1 M ethanolamine pH8.5 for 10 min.

Antibodies were analyzed in Single Cycle Kinetics (SCK) on CD127 to determine kinetic and affinity parameters. The surface functionalized with CD127-Fc was regenerated between each cycle by injection of a 4 M MgCl 2 solution for 30 seconds.

The results presented in table 2 show that the Effi3 antibody is much less affin to CD127 than the commercial antibody eBioRD5 from 2 log. In the method according to the invention, moderate affinity is a key parameter. In order to recover Teffector cells depleted in Treg cells, an anti-CD127 antibody with a moderate affinity has the advantageous ability to be stripped from T cells more easily, rendering the Effi3 antibody very usefull for an in vitro method for sorting out T effectors cells from a biological sample, and thereafter washing (i.e. stripping) the T cells from the antibody used for sorting out the cells, while a high affinity antibody has the disadvantage to be more difficult to strip. Hence, T cells sorted with a high affinity antibody may still comprise antibodies used during the sorting step, even after washing the sorted cells. Those cells being intented for use in cell therapy for human in need thereof, there is a need for a formulation as pure as possible, i.e. not comprising the antibodies used during the method for sorting out the Teffector cells.

TABLE 2

Anti-CD127 antibodies affinity for CD127 protein.

| | Kd1 | Ka1 | KD (M) (BIVALENT model) |
|---|---|---|---|
| eBioRDR5 | 1.48E−05 | 2.71E+05 | 6.83E−11 |
| Effi3_VH3VL3 | 2.15E−04 | 1.33E+05 | 1.62E−09 |

Antibody Selection Based on Antagonist/Agonist Capacities

Positive cell sorting targeted at CD127 has potentially an unwanted activity: it might prevent binding of IL-7 to its receptor and therefore reduce T cell reactivity after sorting.

This is unwanted in a context where sorted T cells need to be re-injected in patients to exert their immune activity.

Therefore, antibodies Effi-3, eBIORDR5 and hIL7R-M21 were compared; their potential to inhibit IL-7 mediated signal in T cells has been evaluated by analyzing the phosphorylation of STAT5 by flow cytometry.

Human PBMC were extracted from the blood of healthy donors (EFS, Nantes) by Ficoll gradient centrifugation (GE Healthcare Life Science, Paris, France). Red blood cells were then lyzed (SOP Eq3 N°S20) and washed before reconstitution at appropriate concentration in culture media. Cells were cultured in a 96-plate with different concentrations of Effi3 clone VH3VL3, eBioRDR5 or hIL7R-M21 during 30 minutes at 37° C., 5% CO2 in serum-free medium. Then, PBMC were stimulated by addition of recombinant human IL-7 at 10 ng/ml (FIG. 1A) or 0.1 ng/ml (FIG. 1B) for 15 min at 37° C. CD3+ cells were stained with fluorochrome-labelled anti-CD3 antibody to gate on T cells. After permeabilization, P-STAT5 molecule were detected with APC-labelled anti-pSTAT5 antibody (BD). PBMC untreated with rhIL-7 were analyzed as the background signal.

The data presented FIG. 1 demonstrated that eBIORDR5 and hIL7R-M21 commercial antibodies antagonize the biological activity of IL-7, whereas Effi-3 does not modify the phosphorylation of STAT5 induced by IL7 like the isotype control, indicating that Effi3 antibody does not interfere with IL7-pathway.

Cell Sorting Capacities of Selected Antibodies

EFFI7-1 and EFFI7-3 antibodies have been biotinylated for use in magnetic cell sorting, using antibiotin-magnetic beads and the MACS cell sorting system (Miltenyi) according to the manufacturer's instructions. Three independent sorting have been realized, illustrated in Table 3. The data showed an equivalence between EFFI7-1 and EFFI7-3 antibodies for the yield and the purity of the Teff sorted cells. A tendency for better results with antibody EFFI7-3 has been recorded.

TABLE 3

| Cell Sorting experiment # | Antibody | Purity in CD127+ cells (%) | Yield (%) | % depletion of CD127lowFoxP3+ Treg cells |
|---|---|---|---|---|
| 1 | EFFI7-1 | 89.3 | 56.33 | 92.57 |
|   | EFFI7-3 | 91.1 | 51.45 | 93.2 |
| 2 | EFFI7-1 | 86.1 | 53.45 | 94.88 |
|   | EFFI7-3 | 86.7 | 54.84 | 95.17 |
| 3 | EFFI7-1 | 89.4 | 51.84 | 88.74 |
|   | EFFI7-3 | 89.6 | 52.44 | 96.22 | sorted cells have been counted and analyzed by flow cytometry with anti-CD3, CD127 and FoxP3 antibodies Effi-3 (the humanized version of Effi7-3) has been compared with the humanized version of the Effi7-2 antibody (described in WO 2015/189302), an antibody known to possess antagonist activity towards IL-7, but used here as a matter of comparison because EFFI7-2 and its humanized version have a very high affinity (see Table 1). Surprisingly, even though humanized EFFI7-2 could bind target cells with a higher efficacy than Effi-3 (FIG. 2), Effi-3 performed better in cell sorting. Indeed, use of biotinylated Effi-3 in the cell sorting process led to a purity in CD127+ cells of 73.9% with a yield of 55.36% and a depletion in FoxP3+ Treg cells of 99.9%. In comparison, use of biotinylated humanized EFFI7-2 in the cell sorting process led to a purity in CD127+ cells of 59.2% with a yield of 17.15% and a depletion in FoxP3+ Treg cells of 99.5% (Table 4).

TABLE 4

Outcomes of cell sorting of CD127+ cells using MACS Cell Sorter (Miltenyi) apparatus using Humanized EFFI7-2 or Effi-3 antibodies.

| Antibody | Purity of CD127+ cells (%) | Yield (%) | Depletion of CD127lowFoxP3+ Treg cells |
|---|---|---|---|
| Humanized EFFI7-2 | 59.2 | 17.15 | 99.5 |
| Effi-3 | 73.9 | 55.36 | 99.9 |

To improve the sorting parameters using biotinylated Effi-3, we added Tegeline (LFB) as a blocking agent in the staining process. Tegeline is a commercial preparation of human immunoglobulins used here to reducing nonspecific interactions of the Effi-3 antibody with target cells and to improve the purity of sorted target cells. We tested two doses of Tegeline: 10 and 250 micrograms. These sorting trials demonstrated that addition of Tegeline in the sorting process improved purity of sorted cells and, more surprisingly, improved the yield (Tables 5 and 6). The % of depletion of Treg cells stayed very high (FIG. 3).

TABLE 5

Outcomes of cell sorting of CD127+ cells using Effi-3 antibodies together with Tegeline (one experiment).

| Effi-3 together with tegeline | Purity of CD127+ cells (%) | Yield (%) | Depletion of CD127lowFoxP3+ Treg cells |
|---|---|---|---|
| Tegeline 10 µg | 87.7 | 50.3 | 97.7 |
| Tegeline 250 µg | 87.7 | 58.23 | 94.3 |

TABLE 6

Outcomes of cell sorting of CD127+ cells using Effi-3 antibodies together with Tegeline (mean of data from 3 experiments)

| Effi-3 together with tegeline | Purity of CD127+ cells (%) | Yield (%) | Depletion of CD127lowFoxP3+ Treg cells |
|---|---|---|---|
| Tegeline 10 µg | 87.2 | 47.8 | 90.5 |
| Tegeline 250 µg | 86.7 | 43.1 | 91.4 |

Conclusion

Sorting out active Treg cells from T cell preparations is useful in cell therapies where Teff cells need to mount an immune response against a target, most frequently a tumor. CD127 is a target expressed on Teff and less on Treg, opening the possibility to differentially bind to and sort out Teff from Treg. We have shown that Effi-3, in particular Effi3-VH3VL3, are good antibodies able to bind to and sort out Teff cells using a Macs system, even though this antibody shows a moderate binding affinity. Other available antibodies are good binders of CD127+ cells and might be used to sort out Teff cells, such as eBIORDR5 or humanized EFFI7-2. However, eBIORDR5 and humanized EFFI7-2 are antagonist antibodies preventing T cell responses induced by IL-7. Their use might therefore likely compromise immune responses that are required for the efficacy of Teff transfer. In addition, humanized EFFI7-2 in spite of its very high affinity resulted in a poor sorting yields. Thus Effi-3 antibodies are suitable for cell sorting in the conditions described here because they show efficacy in sorting out target CD127$^+$ cells and lack antagonist activity to IL-7.

The following table (Table 7) discloses the sequence described herein. "Nb" stands for the SEQ ID NO of each sequence; "Type" discloses the nature of the sequence, either DNA or amino acid sequence (PRT).

The sequences of the specific domains of the antibodies are provided in reference to the Kabat nomenclature.

| Nb | Nom | Type | Séquence |
|---|---|---|---|
| 1 | Effi3 VH3 | DNA | GCTGTGCAGCTGGTCGAATCTGGGGGGGGCTGGTCCAGCCCGGCGGGTC TCTGAAAATCACTTGCGCCGCTAGTGGGTTCACCTTTACAAACGCAGCCA TGTACTGGGTCCGACAGGCTCCTGGAAAGGGCCTGGAGTGGGTGGCACGG ATCAGAACAAAGGCTAACAACTACGCAACTTACTATGCCGACTCAGTGAA GGGCAGGTTCACCATTAGCCGCGACGATAGCAAATCCACAGTCTACCTGC AGATGGACTCTGTGAAGACAGAAGATACTGCCACCTACTATTGTATTGTG GTCGTGCTGACTACTACACGGGATTACTTTGACTATTGGGGACAGGGAGT GCTGGTGACAGTGAGTTCA |
| 2 | Effi3 VH3_aa | PRT | AVQLVESGGGLVQPGGSLKITCAASGFTFTNAAMYWVRQAPGKGLEWVAR IRTKANNYATYYADSVKGRFTISRDDSKSTVYLQMDSVKTEDTATYYCIV VVLTTTRDYFDYWGQGVLVTVSS |
| 3 | Effi3 VL3 | DNA | GACATCGTCCTGACTCAGTCCCCCTCTTCCCTGCCAGTGACACCTGGAGA GCCAGCATCTATCAGTTGCCGAAGCTCCCAGTCACTGCTGACTGTCAAGG GAATTACCAGCCTGTACTGGTTCCTGCAGAAGCCCGGCCAGTCCCCTAAA CTGCTGATCTATCGGATGTCTAACAGAGACAGTGGGGTGCCCGATAGGTT CTCAGGCAGCGGGTCCGAAACCGACTTTACACTGAAAATTTCTCGCGTGG AGGCTGAAGATGTCGGAACCTACTATTGCGCACAGTTTCTGGAATACCCT CACACTTTCGGGGCAGGCACTAAGCTGGAGCTGAAGCGT |
| 4 | Effi3 VL3_aa | PRT | DIVLTQSPSSLPVTPGEPASISCRSSQSLLTVKGITSLYWFLQKPGQSPK LLIYRMSNRDSGVPDRFSGSGSETDFTLKISRVEAEDVGTYYCAQFLEYP HTFGAGTKLELKR |
| 5 | Effi3 VL4 | DNA | GACATCGTGCTGACACAGAGTCCCTCCTCCCTGCCAGTGACACCTGGAGA GCCAGCATCTATCAGTTGCCGAAGCTCCCAGGACCTGCTGACTGTCAAGG GCATTACCTCACTGTACTGGTTCCTGCAGAAGCCCGGCCAGAGCCCTAAA CTGCTGATCTATCGGATGTCTAACAGAGACAGTGGAGTGCCCGATAGGTT CTCAGGCAGCGGGTCCGGAACCGACTTTACACTGAAAATTTCTCGCGTGG AGGCTGAAGATGTCGGCACCTACTATTGCGCACAGTTTCTGGAGTATCCC CACACCTTTGGAGCAGGCACTAAGCTGGAGCTGAAGCGT |
| 6 | Effi3 VL4_aa | PRT | DIVLTQSPSSLPVTPGEPASISCRSSQDLLTVKGITSLYWFLQKPGQS PKLLIYRMSNRDSGVPDRFSGSGSGTDFTLKISRVEAEDVGTYYCAQFLE YPHTFGAGTKLELKR |
| 7 | Effi3 VH3 (+signal peptide) | DNA | ATGCTGGTCCTGCAGTGGGTCCTGGTCACCGCTCTGTTTCAGGGGGTCCA TTGTGCTGTGCAGCTGGTCGAATCTGGGGGGGGCTGGTCCAGCCCGGCG GTCTCTGAAAATCACTTGCGCCGCTAGTGGGTTCACCTTTACAAACGCA GCCATGTACTGGGTCCGACAGGCTCCTGGAAAGGGCCTGGAGTGGGTGGC ACGGATCAGAACAAAGGCTAACAACTACGCAACTTACTATGCCGACTCAG TGAAGGGCAGGTTCACCATTAGCCGCGACGATAGCAAATCCACAGTCTAC CTGCAGATGGACTCTGTGAAGACAGAAGATACTGCCACCTACTATTGTAT TGTGGTCGTGCTGACTACTACACGGGATTACTTTGACTATTGGGGACAGG GAGTGCTGGTGACAGTGAGTTCA |
| 8 | Effi3 VH3_aa (+signal peptide) | PRT | MLVLQWVLVTALFQGVHCAVQLVESGGGLVQPGGSLKITCAASGFTFTNA AMYWVRQAPGKGLEWVARIRTKANNYATYYADSVKGRFTISRDDSKSTVY LQMDSVKTEDTATYYCIVVVLTTTRDYFDYWGQGVLVTVSS |
| 9 | Effi3 VL3 (+signal peptide) | DNA | ATGAAGTTTCCTGCTCAGTTTCTGGGCCTGATTGTGCTGTGTATTCCTGG CGCTACCGGAGACATCGTCCTGACTCAGTCCCCCTCTTCCCTGCCAGTGA CACCTGGAGAGCCAGCATCTATCAGTTGCCGAAGCTCCCAGTCACTGCTG ACTGTCAAGGGAATTACCAGCCTGTACTGGTTCCTGCAGAAGCCCGGCCA GTCCCCTAAACTGCTGATCTATCGGATGTCTAACAGAGACAGTGGGGTGC CCGATAGGTTCTCAGGCAGCGGGTCCGAAACCGACTTTACACTGAAAATT TCTCGCGTGGAGGCTGAAGATGTCGGAACCTACTATTGCGCACAGTTTCT GGAATACCCTCACACTTTCGGGGCAGGCACTAAGCTGGAGCTGAAGCGT |
| 10 | Effi3 VL3_aa (+signal peptide) | PRT | MKFPAQFLGLIVLCIPGATGDIVLTQSPSSLPVTPGEPASISCRSSQSLL TVKGITSLYWFLQKPGQSPKLLIYRMSNRDSGVPDRFSGSGSETDFTLKI SRVEAEDVGTYYCAQFLEYPHTFGAGTKLELKR |

| Nb | Nom | Type | Séquence |
|----|-----|------|----------|
| 11 | Effi3 VL4 (+signal peptide) | DNA | ATGAAGTTCCCTGCTCAGTTCCTGGGGCTGATTGTCCTGTGCATTCCTGG GGCAACCGGCGACATCGTGCTGACACAGAGTCCCTCCTCCCTGCCAGTGA CACCTGGAGAGCCAGCATCTATCAGTTGCCGAAGCTCCCAGGACCTGCTG ACTGTCAAGGGCATTACCTCACTGTACTGGTTCCTGCAGAAGCCCGGGCA GAGCCCTAAACTGCTGATCTATCGGATGTCTAACAGAGACAGTGGAGTGC CCGATAGGTTCTCAGGCAGCGGGTCCGGAACCGACTTTACACTGAAAATT TCTCGCGTGGAGGCTGAAGATGTCGGCACCTACTATTGCGCACAGTTTCT GGAGTATCCCCACACCTTTGGAGCAGGCACTAAGCTGGAGCTGAAGCGT |
| 12 | Effi3 VL4_aa (+signal peptide) | PRT | MKFPAQFLGLIVLCIPGATGDIVLTQSPSSLPVTPGEPASISCRSSQDLL TVKGITSLYWFLQKPGQSPKLLIYRMSNRDSGVPDRFSGSGSGTDFTLKI SRVEAEDVGTYYCAQFLEYPHTFGAGTKLELKR |
| 13 | Effi3 VH3_CDR1 | DNA | TTCACCTTTACAAACGCAGCCATGTAC |
| 14 | Effi3 VH3_CDR1 aa | PRT | FTFTNAAMY |
| 15 | Effi3 VH3_CDR2 | DNA | CGGATCAGAACAAAGGCTAACAACTACGCAACTTACTATGCCGACTCAGT GAAGGGC |
| 16 | Effi3 VH3_CDR2 aa | PRT | RIRTKANNYATYYADSVKG |
| 17 | Effi3 VH3_CDR3 | DNA | GTCGTGCTGACTACTACACGGGATTACTTTGACTAT |
| 18 | Effi3 VH3_CDR3 aa | PRT | VVLTTTRDYFDY |
| 19 | Effi3 VL3_CDR1 | DNA | CGAAGCTCCCAGTCACTGCTGACTGTCAAGGGAATTACCAGCCTGTAC |
| 20 | Effi3 VL3 CDR1_aa | PRT | RSSQSLLTVKGITSLY |
| 21 | Effi3 VL3/4_CDR2 | DNA | CGGATGTCTAACAGAGACAGT |
| 22 | Effi3 VL3/4_CDR2aa | PRT | RMSNRDS |
| 23 | Effi3 VL3/4_CDR3 | DNA | GCACAGTTTCTGGAATACCCTCACACT |
| 24 | Effi3 VL3/4_CDR3aa | PRT | AQFLEYPHT |
| 25 | Effi3 VL4_CDR1 | DNA | CGAAGCTCCCAGGACCTGCTGACTGTCAAGGGCATTACCTCACTGTAC |
| 26 | Effi3 VL4_CDR1_aa | PRT | RSSQDLLTVKGITSLY |

REFERENCES

Horowitz M M, et al. Graftversus—leukemia reactions after bone marrow transplantation. Blood. 1990; 75(3): 555-62

Martin P J. Increased disparity for minor histocompatibility antigens as a potential cause of increased GVHD risk in marrow transplantation from unrelated donors compared with related donors. Bone Marrow Transplant. 1991; 8(3):217-23

Nishikawa H, Sakaguchi S. Regulatory T cells in tumor immunity. Int J Cancer. 2010; 127(4):759-67

Cohen J L, Boyer O. The role of CD4+CD25hi regulatory T cells in the Physiopathogeny of graft-versus-host disease. Curr Opin Immunol. 2006; 18(5):580-5

Hicheri Y, et al. Donor regulatory T cells identified by FoxP3 expression but also by the membranous CD4+ CD127low/neg phenotype influence graft-versus-tumor effect after donor lymphocyte infusion. J Immunother. 2008; 31(9):806-11

Maury et al, CD4+CD25+ regulatory T cell depletion improves the graft-versus-tumor effect of donor lymphocytes after allogeneic hematopoietic stem cell transplantation. Sci Transl Med. 2010 Jul. 21; 2(41):41ra52

Touil et al, Depletion of T regulatory cells through selection of CD127-positive cells results in a population enriched in memory T cells: implications for anti-tumor cell therapy. Haematologica. 2012 November; 97(11): 1678-1685

Giraldo et al, Tumor-Infiltrating and Peripheral Blood T-cell Immunophenotypes Predict Early Relapse in Localized Clear Cell Renal Cell Carcinoma. Clin Cancer Res. 2017 Feb. 17

What is claimed is:

1. A method for in vitro sorting out T effector cells from a preparation of cells obtained from a biological fluid or tissue wherein the preparation of cells comprises human cells, wherein the method comprises:
   a. contacting the preparation of cells with an anti-CD127 antibody specifically binding to CD127 on said T effector cells, said anti-CD127 antibody comprising the following CDRs sequences:
      in a heavy chain, CDRs of a VH3 heavy chain disclosed as sequence of SEQ ID No: 2, with CDRs of VH3-CDR1, VH3-CDR2 and VH3-CDR3 comprising or consisting of sequences of SEQ ID Nos: 14, 16 and 18, respectively and,
      in a light chain, CDRs of a VL3 or of a VL4 light chain disclosed as sequences of SEQ ID Nos: 4 and 6, respectively, with CDRs VL3-CDR1, VL3/4-CDR2 and VL3/4-CDR3 having the sequences of SEQ ID Nos: 20, 22 and 24 respectively, or with CDRs of VL4-CDR1, VL3/4-CDR2 and VL3/4-CDR3 comprising or consisting of the sequences of SEQ ID Nos: 26, 22 and 24 respectively;
   b. selecting sorting out said T effector cells bound to said anti-CD127 antibody and recovering the cell preparation enriched in said T effector cells and depleted for at least Treg cells;
   washing the anti-CD127 antibody from said T effector cells.

2. The method according to claim 1, wherein the anti-CD127 antibody is selected from anti-CD127 antibodies comprising VH and VL sequences as follows: a. a heavy chain variable domain designated Effi3-VH3 comprising or consisting of sequence of SEQ ID No: 2 or Effi3-VH3 variant comprising or consisting of sequence SEQ ID No: 8 and,
   for a variant designated Effi3-VH3VL3, either a light chain variable domain designated Effi3-VL3 comprising or consisting of sequence SEQ ID No: 4 or Effi3-VL3 variant comprising or consisting of sequence SEQ ID No: 10, or alternatively b. a heavy chain variable domain designated Effi3-VH3 comprising or consisting of sequence of SEQ ID No: 2 or Effi3-VH3 variant comprising or consisting of sequence SEQ ID No: 8 and,
   for a variant designated Effi3-VH3VL4, either a light chain variable domain designated Effi3-VL4 comprising or consisting of sequence SEQ ID No: 6 or Effi3-VL4 variant comprising or consisting of sequence SEQ ID No: 12.

3. The method according to claim 1, wherein the step of sorting out cells is performed using magnetic cell sorting and the anti-CD127 antibody is biotinylated or otherwise marked for staining.

4. The method according to claim 1, wherein cell sorting is performed until more than 90% of Treg cells are depleted from the preparation of cells.

5. The method of claim 4 wherein more than 99% of Treg cells are depleted from the preparation of cells.

6. The method according to claim 1, wherein the anti-CD127 antibodies is provided with a composition that comprises polyclonal immunoglobulins suitable for reducing nonspecific interactions of the anti-CD127 antibody with targeted T effector cells.

7. The method according to claim 1, wherein the cell preparation is a human blood cell preparation.

8. The method according to claim 1, wherein the cell preparation is a preparation of hematopoietic stem cells for transplantation (HSCT) or T cells for adoptive therapy.

9. The method according to claim 8 wherein the cell preparation includes T cells for adoptive therapy selected from the group consisting of tumor-infiltrating cells (TILs), genetically modified cancer-specific T cells known as Chimeric-Antigen Receptor T cells (CART), or both.

10. The method according to claim 1, further comprising administering the T effector cells to a human patient to treat a solid or liquid tumor in the human patient or administering the T effector cells to a human patient to treat a chronic infection by a pathogen selected among bacteria, parasites, protozoans, yeasts and viruses.

11. The method according to claim 10, wherein the anti-CD127 antibody is selected from anti-CD127 antibodies comprising VH and VL sequences as follows: a. a heavy chain variable domain designated Effi3-VH3 comprising or consisting of sequence of SEQ ID No: 2 or Effi3-VH3 variant comprising or consisting of sequence SEQ ID No: 8 and, for a variant designated Effi3-VH3VL3, either a light chain variable domain designated Effi3-VL3 comprising or consisting of sequence SEQ ID No: 4 or Effi3-VL3 variant comprising or consisting of sequence SEQ ID No: 10, or alternatively b. a heavy chain variable domain designated Effi3-VH3 comprising or consisting of sequence of SEQ ID No: 2 or Effi3-VH3 variant comprising or consisting of sequence SEQ ID No: 8 and, for a variant designated Effi3-VH3VL4, either a light chain variable domain designated Effi3-VL4 comprising or consisting of sequence SEQ ID No: 6 or Effi3-VL4 variant comprising or consisting of sequence SEQ ID No: 12.

12. The method according to claim 10, wherein the step of sorting out cells is performed using magnetic cell sorting and the anti-CD127 antibody is biotinylated or otherwise marked for staining.

13. The method according to claim 10, wherein cell sorting is performed until more than 90% of Treg cells are depleted from the preparation of cells.

14. The method according to claim 10, wherein the anti-CD127 antibodies is provided with a composition that comprises polyclonal immunoglobulins suitable for reducing nonspecific interactions of the anti-CD127 antibody with targeted T effector cells.

15. The method according to claim 1 wherein the anti-CD127 antibody is an antibody that does not compete with interleukin-7 for binding to an interleukin-7 (IL-7) receptor.

* * * * *

SEQUENCE LISTING

<160> NUMBER OF SEQ ID NOS: 26

<210> SEQ ID NO 1
<211> LENGTH: 369
<212> TYPE: DNA
<213> ORGANISM: Artificial Sequence
<220> FEATURE:

<223> OTHER INFORMATION: Effi3 VH3

<400> SEQUENCE: 1

| gctgtgcagc | tggtcgaatc | tggggggggg | ctggtccagc | ccggcgggtc | tctgaaaatc | 60 |
| acttgcgccg | ctagtgggtt | cacctttaca | aacgcagcca | tgtactggt | ccgacaggct | 120 |
| cctggaaagg | gcctggagtg | ggtggcacgg | atcagaacaa | aggctaacaa | ctacgcaact | 180 |
| tactatgccg | actcagtgaa | gggcaggttc | accattagcc | gcgacgatag | caaatccaca | 240 |
| gtctacctgc | agatggactc | tgtgaagaca | gaagatactg | ccacctacta | ttgtattgtg | 300 |
| gtcgtgctga | ctactacacg | ggattacttt | gactattggg | gacagggagt | gctggtgaca | 360 |
| gtgagttca | | | | | | 369 |

<210> SEQ ID NO 2
<211> LENGTH: 123
<212> TYPE: PRT
<213> ORGANISM: Artificial Sequence
<220> FEATURE:
<223> OTHER INFORMATION: Effi3 VH3_aa

<400> SEQUENCE: 2

Ala Val Gln Leu Val Glu Ser Gly Gly Gly Leu Val Gln Pro Gly Gly
1               5                   10                  15

Ser Leu Lys Ile Thr Cys Ala Ala Ser Gly Phe Thr Phe Thr Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Ala Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asp Ser Val Lys Thr Glu Asp Thr Ala Thr Tyr
                85                  90                  95

Tyr Cys Ile Val Val Val Leu Thr Thr Thr Arg Asp Tyr Phe Asp Tyr
            100                 105                 110

Trp Gly Gln Gly Val Leu Val Thr Val Ser Ser
        115                 120

<210> SEQ ID NO 3
<211> LENGTH: 339
<212> TYPE: DNA
<213> ORGANISM: Artificial Sequence
<220> FEATURE:
<223> OTHER INFORMATION: Effi3 VL3

<400> SEQUENCE: 3

| gacatcgtcc | tgactcagtc | ccctcttcc | ctgccagtga | cacctggaga | gccagcatct | 60 |
| atcagttgcc | gaagctccca | gtcactgctg | actgtcaagg | gaattaccag | cctgtactgg | 120 |
| ttcctgcaga | agcccggcca | gtcccctaaa | ctgctgatct | atcggatgtc | taacagagac | 180 |
| agtggggtgc | ccgataggtt | ctcaggcagc | gggtccgaaa | ccgactttac | actgaaaatt | 240 |
| tctcgcgtgg | aggctgaaga | tgtcggaacc | tactattgcg | cacagtttct | ggaatacct | 300 |
| cacactttcg | gggcaggcac | taagctggag | ctgaagcgt | | | 339 |

<210> SEQ ID NO 4
<211> LENGTH: 113
<212> TYPE: PRT
<213> ORGANISM: Artificial Sequence
<220> FEATURE:
<223> OTHER INFORMATION: Effi3 VL3_aa

<400> SEQUENCE: 4

Asp Ile Val Leu Thr Gln Ser Pro Ser Ser Leu Pro Val Thr Pro Gly
1               5                   10                  15

Glu Pro Ala Ser Ile Ser Cys Arg Ser Ser Gln Ser Leu Leu Thr Val
            20                  25                  30

Lys Gly Ile Thr Ser Leu Tyr Trp Phe Leu Gln Lys Pro Gly Gln Ser
        35                  40                  45

Pro Lys Leu Leu Ile Tyr Arg Met Ser Asn Arg Asp Ser Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Thr Tyr Tyr Cys Ala Gln Phe
                85                  90                  95

Leu Glu Tyr Pro His Thr Phe Gly Ala Gly Thr Lys Leu Glu Leu Lys
            100                 105                 110

Arg

<210> SEQ ID NO 5
<211> LENGTH: 339
<212> TYPE: DNA
<213> ORGANISM: Artificial Sequence
<220> FEATURE:
<223> OTHER INFORMATION: Effi3 VL4

<400> SEQUENCE: 5
gacatcgtgc tgacacagag tccctcctcc ctgccagtga cacctggaga gccagcatct      60
atcagttgcc gaagctccca ggacctgctg actgtcaagg gcattacctc actgtactgg     120
ttcctgcaga agcccgggca gagccctaaa ctgctgatct atcggatgtc taacagagac     180
agtggagtgc ccgataggtt ctcaggcagc gggtccggaa ccgactttac actgaaaatt     240
tctcgcgtgg aggctgaaga tgtcggcacc tactattgcg cacagtttct ggagtatccc     300
cacacctttg gagcaggcac taagctggag ctgaagcgt                            339

<210> SEQ ID NO 6
<211> LENGTH: 113
<212> TYPE: PRT
<213> ORGANISM: Artificial Sequence
<220> FEATURE:
<223> OTHER INFORMATION: Effi3 VL4_aa

<400> SEQUENCE: 6

Asp Ile Val Leu Thr Gln Ser Pro Ser Ser Leu Pro Val Thr Pro Gly
1               5                   10                  15

Glu Pro Ala Ser Ile Ser Cys Arg Ser Ser Gln Asp Leu Leu Thr Val
            20                  25                  30

Lys Gly Ile Thr Ser Leu Tyr Trp Phe Leu Gln Lys Pro Gly Gln Ser
        35                  40                  45

Pro Lys Leu Leu Ile Tyr Arg Met Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ala Gln Phe
                85                  90                  95

Leu Glu Tyr Pro His Thr Phe Gly Ala Gly Thr Lys Leu Glu Leu Lys

<210> SEQ ID NO 7
<211> LENGTH: 423
<212> TYPE: DNA
<213> ORGANISM: Artificial Sequence
<220> FEATURE:
<223> OTHER INFORMATION: Effi3 VH3 (+signal peptide)

<400> SEQUENCE: 7

```
atgctggtcc tgcagtgggt cctggtcacc gctctgtttc aggggtcca ttgtgctgtg      60
cagctggtcg aatctggggg ggggctggtc cagcccggcg ggtctctgaa aatcacttgc    120
gccgctagtg ggttcacctt tacaaacgca gccatgtact gggtccgaca ggctcctgga    180
aagggcctgg agtgggtggc acggatcaga acaaaggcta acaactacgc aacttactat    240
gccgactcag tgaagggcag gttcaccatt agccgcgacg atagcaaatc cacagtctac    300
ctgcagatgg actctgtgaa gacagaagat actgccacct actattgtat tgtggtcgtg    360
ctgactacta cacgggatta ctttgactat tggggacagg gagtgctggt gacagtgagt    420
tca                                                                 423
```

<210> SEQ ID NO 8
<211> LENGTH: 141
<212> TYPE: PRT
<213> ORGANISM: Artificial Sequence
<220> FEATURE:
<223> OTHER INFORMATION: Effi3 VH3_aa (+signal peptide)

<400> SEQUENCE: 8

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Gly Gly Ser Leu Lys Ile Thr Cys Ala Ala Ser Gly Phe Thr Phe Thr
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Ala Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Thr Val Tyr Leu Gln Met Asp Ser Val Lys Thr Glu Asp Thr Ala
            100                 105                 110

Thr Tyr Tyr Cys Ile Val Val Val Leu Thr Thr Thr Arg Asp Tyr Phe
        115                 120                 125

Asp Tyr Trp Gly Gln Gly Val Leu Val Thr Val Ser Ser
    130                 135                 140

<210> SEQ ID NO 9
<211> LENGTH: 399
<212> TYPE: DNA
<213> ORGANISM: Artificial Sequence
<220> FEATURE:
<223> OTHER INFORMATION: Effi3 VL3 (+signal peptide)

<400> SEQUENCE: 9

```
atgaagtttc ctgctcagtt tctgggcctg attgtgctgt gtattcctgg cgctaccgga      60
```

```
gacatcgtcc tgactcagtc ccctcttcc ctgccagtga cacctggaga gccagcatct      120
atcagttgcc gaagctccca gtcactgctg actgtcaagg gaattaccag cctgtactgg      180
ttcctgcaga agcccggcca gtcccctaaa ctgctgatct atcggatgtc taacagagac      240
agtggggtgc ccgataggtt ctcaggcagc gggtccgaaa ccgactttac actgaaaatt      300
tctcgcgtgg aggctgaaga tgtcggaacc tactattgcg cacagtttct ggaataccct      360
cacactttcg gggcaggcac taagctggag ctgaagcgt                            399
```

```
<210> SEQ ID NO 10
<211> LENGTH: 133
<212> TYPE: PRT
<213> ORGANISM: Artificial Sequence
<220> FEATURE:
<223> OTHER INFORMATION: Effi3 VL3_aa (+signal peptide)

<400> SEQUENCE: 10
```

```
Met Lys Phe Pro Ala Gln Phe Leu Gly Leu Ile Val Leu Cys Ile Pro
1               5                   10                  15

Gly Ala Thr Gly Asp Ile Val Leu Thr Gln Ser Pro Ser Ser Leu Pro
            20                  25                  30

Val Thr Pro Gly Glu Pro Ala Ser Ile Ser Cys Arg Ser Ser Gln Ser
        35                  40                  45

Leu Leu Thr Val Lys Gly Ile Thr Ser Leu Tyr Trp Phe Leu Gln Lys
    50                  55                  60

Pro Gly Gln Ser Pro Lys Leu Leu Ile Tyr Arg Met Ser Asn Arg Asp
65                  70                  75                  80

Ser Gly Val Pro Asp Arg Phe Ser Gly Ser Gly Ser Glu Thr Asp Phe
                85                  90                  95

Thr Leu Lys Ile Ser Arg Val Glu Ala Glu Asp Val Gly Thr Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg
    130
```

```
<210> SEQ ID NO 11
<211> LENGTH: 399
<212> TYPE: DNA
<213> ORGANISM: Artificial Sequence
<220> FEATURE:
<223> OTHER INFORMATION: Effi3 VL4 (+signal peptide)

<400> SEQUENCE: 11
```

```
atgaagttcc ctgctcagtt cctggggctg attgtcctgt gcattcctgg ggcaaccggc       60
gacatcgtgt gcacacagag tccctcctcc ctgccagtga cacctggaga gccagcatct      120
atcagttgcc gaagctccca ggacctgctg actgtcaagg gcattacctc actgtactgg      180
ttcctgcaga agcccgggca gagccctaaa ctgctgatct atcggatgtc taacagagac      240
agtggagtgc ccgataggtt ctcaggcagc gggtccggaa ccgactttac actgaaaatt      300
tctcgcgtgg aggctgaaga tgtcggcacc tactattgcg cacagtttct ggagtatccc      360
cacacctttg gagcaggcac taagctggag ctgaagcgt                            399
```

```
<210> SEQ ID NO 12
<211> LENGTH: 133
<212> TYPE: PRT
<213> ORGANISM: Artificial Sequence
<220> FEATURE:
```

<223> OTHER INFORMATION: Effi3 VL4_aa (+signal peptide)

<400> SEQUENCE: 12

Met Lys Phe Pro Ala Gln Phe Leu Gly Leu Ile Val Leu Cys Ile Pro
1               5                   10                  15

Gly Ala Thr Gly Asp Ile Val Leu Thr Gln Ser Pro Ser Ser Leu Pro
            20                  25                  30

Val Thr Pro Gly Glu Pro Ala Ser Ile Ser Cys Arg Ser Ser Gln Asp
        35                  40                  45

Leu Leu Thr Val Lys Gly Ile Thr Ser Leu Tyr Trp Phe Leu Gln Lys
    50                  55                  60

Pro Gly Gln Ser Pro Lys Leu Leu Ile Tyr Arg Met Ser Asn Arg Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Thr Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg
    130

<210> SEQ ID NO 13
<211> LENGTH: 27
<212> TYPE: DNA
<213> ORGANISM: Artificial Sequence
<220> FEATURE:
<223> OTHER INFORMATION: Effi3 VH3_CDR1

<400> SEQUENCE: 13
ttcaccttta caaacgcagc catgtac                                27

<210> SEQ ID NO 14
<211> LENGTH: 9
<212> TYPE: PRT
<213> ORGANISM: Artificial Sequence
<220> FEATURE:
<223> OTHER INFORMATION: Effi3 VH3_CDR1 aa

<400> SEQUENCE: 14

Phe Thr Phe Thr Asn Ala Ala Met Tyr
1               5

<210> SEQ ID NO 15
<211> LENGTH: 57
<212> TYPE: DNA
<213> ORGANISM: Artificial Sequence
<220> FEATURE:
<223> OTHER INFORMATION: Effi3 VH3_CDR2

<400> SEQUENCE: 15
cggatcagaa caaaggctaa caactacgca acttactatg ccgactcagt gaagggc    57

<210> SEQ ID NO 16
<211> LENGTH: 19
<212> TYPE: PRT
<213> ORGANISM: Artificial Sequence
<220> FEATURE:
<223> OTHER INFORMATION: Effi3 VH3_CDR2 aa

<400> SEQUENCE: 16

Arg Ile Arg Thr Lys Ala Asn Asn Tyr Ala Thr Tyr Tyr Ala Asp Ser

Val Lys Gly

<210> SEQ ID NO 17
<211> LENGTH: 36
<212> TYPE: DNA
<213> ORGANISM: Artificial Sequence
<220> FEATURE:
<223> OTHER INFORMATION: Effi3 VH3_CDR3

<400> SEQUENCE: 17
gtcgtgctga ctactacacg ggattacttt gactat                                 36

<210> SEQ ID NO 18
<211> LENGTH: 12
<212> TYPE: PRT
<213> ORGANISM: Artificial Sequence
<220> FEATURE:
<223> OTHER INFORMATION: Effi3 VH3_CDR3 aa

<400> SEQUENCE: 18

Val Val Leu Thr Thr Thr Arg Asp Tyr Phe Asp Tyr
1               5                   10

<210> SEQ ID NO 19
<211> LENGTH: 48
<212> TYPE: DNA
<213> ORGANISM: Artificial Sequence
<220> FEATURE:
<223> OTHER INFORMATION: Effi3 VL3_CDR1

<400> SEQUENCE: 19
cgaagctccc agtcactgct gactgtcaag ggaattacca gcctgtac                    48

<210> SEQ ID NO 20
<211> LENGTH: 16
<212> TYPE: PRT
<213> ORGANISM: Artificial Sequence
<220> FEATURE:
<223> OTHER INFORMATION: Effi3 VL3_CDR1_aa

<400> SEQUENCE: 20

Arg Ser Ser Gln Ser Leu Leu Thr Val Lys Gly Ile Thr Ser Leu Tyr
1               5                   10                  15

<210> SEQ ID NO 21
<211> LENGTH: 21
<212> TYPE: DNA
<213> ORGANISM: Artificial Sequence
<220> FEATURE:
<223> OTHER INFORMATION: Effi3 VL3/4_CDR2

<400> SEQUENCE: 21
cggatgtcta acagagacag t                                                 21

<210> SEQ ID NO 22
<211> LENGTH: 7
<212> TYPE: PRT
<213> ORGANISM: Artificial Sequence
<220> FEATURE:
<223> OTHER INFORMATION: Effi3 VL3/4_CDR2aa

<400> SEQUENCE: 22

Arg Met Ser Asn Arg Asp Ser
1               5

```
<210> SEQ ID NO 23
<211> LENGTH: 27
<212> TYPE: DNA
<213> ORGANISM: Artificial Sequence
<220> FEATURE:
<223> OTHER INFORMATION: Effi3 VL3/4_CDR3

<400> SEQUENCE: 23
gcacagtttc tggaataccc tcacact                                              27

<210> SEQ ID NO 24
<211> LENGTH: 9
<212> TYPE: PRT
<213> ORGANISM: Artificial Sequence
<220> FEATURE:
<223> OTHER INFORMATION: Effi3 VL3/4_CDR3aa

<400> SEQUENCE: 24

Ala Gln Phe Leu Glu Tyr Pro His Thr
1               5

<210> SEQ ID NO 25
<211> LENGTH: 48
<212> TYPE: DNA
<213> ORGANISM: Artificial Sequence
<220> FEATURE:
<223> OTHER INFORMATION: Effi3 VL4_CDR1

<400> SEQUENCE: 25
cgaagctccc aggacctgct gactgtcaag ggcattacct cactgtac                       48

<210> SEQ ID NO 26
<211> LENGTH: 16
<212> TYPE: PRT
<213> ORGANISM: Artificial Sequence
<220> FEATURE:
<223> OTHER INFORMATION: Effi3 VL4_CDR1_aa

<400> SEQUENCE: 26

Arg Ser Ser Gln Asp Leu Leu Thr Val Lys Gly Ile Thr Ser Leu Tyr
1               5                   10                  15
```